United States Patent
Mouzin et al.

(10) Patent No.: US 9,486,397 B2
(45) Date of Patent: Nov. 8, 2016

(54) DERMOCOSMETIC COMPOSITIONS BASED ON A SYNERGISTIC COMBINATION OF COLLOIDAL SILVER AND DEOXYRIBONUCLEIC ACID

(71) Applicants: Gilbert Mouzin, Castres (FR); Stéphanie Thierry, London (GB); Joy Isaacs, London (GB)

(72) Inventors: Gilbert Mouzin, Castres (FR); Stéphanie Thierry, London (GB); Joy Isaacs, London (GB)

(73) Assignee: ARGENTUM HOLDINGS S.A.R.L., Luxembourg (LU)

( * ) Notice: Subject to any disclaimer, the term of this patent is extended or adjusted under 35 U.S.C. 154(b) by 0 days.

(21) Appl. No.: 14/371,818

(22) PCT Filed: Jan. 10, 2013

(86) PCT No.: PCT/EP2013/050422
§ 371 (c)(1),
(2) Date: Jul. 11, 2014

(87) PCT Pub. No.: WO2013/107687
PCT Pub. Date: Jul. 25, 2013

(65) Prior Publication Data
US 2014/0356436 A1    Dec. 4, 2014

(30) Foreign Application Priority Data

Jan. 16, 2012 (FR) ...................... 12 00122

(51) Int. Cl.
| | | |
|---|---|---|
| *A61K 8/60* | (2006.01) |
| *A61Q 19/08* | (2006.01) |
| *A61K 8/02* | (2006.01) |
| *A61K 8/19* | (2006.01) |
| *A61K 8/49* | (2006.01) |
| *A61Q 1/14* | (2006.01) |
| *A61Q 13/00* | (2006.01) |
| *A61Q 17/04* | (2006.01) |
| *A61Q 19/00* | (2006.01) |
| *A61Q 19/10* | (2006.01) |

(52) U.S. Cl.
CPC ............. *A61K 8/606* (2013.01); *A61K 8/0241* (2013.01); *A61K 8/19* (2013.01); *A61K 8/4953* (2013.01); *A61Q 19/08* (2013.01); *A61K 2800/10* (2013.01); *A61K 2800/413* (2013.01); *A61K 2800/522* (2013.01); *A61K 2800/651* (2013.01); *A61Q 1/14* (2013.01); *A61Q 13/00* (2013.01); *A61Q 17/04* (2013.01); *A61Q 19/001* (2013.01); *A61Q 19/004* (2013.01); *A61Q 19/005* (2013.01); *A61Q 19/008* (2013.01); *A61Q 19/10* (2013.01)

(58) Field of Classification Search
None
See application file for complete search history.

(56) References Cited

U.S. PATENT DOCUMENTS

2010/0055138 A1*  3/2010  Margulies et al. ............ 424/401
2011/0155161 A1*  6/2011  Samain ......................... 132/200

FOREIGN PATENT DOCUMENTS

CH            678487 A  *  9/1991

* cited by examiner

*Primary Examiner* — Susan Tran
(74) *Attorney, Agent, or Firm* — Fish & Tsang LLP

(57) ABSTRACT

The present invention relates to dermocosmetic compositions containing, as active ingredients, a synergistic combination of colloidal silver and deoxyribonucleic acid, characterized in that the colloidal silver is more particularly an aqueous solution of electro colloidal silver.

8 Claims, No Drawings

DERMOCOSMETIC COMPOSITIONS BASED ON A SYNERGISTIC COMBINATION OF COLLOIDAL SILVER AND DEOXYRIBONUCLEIC ACID

The present invention concerns dermocosmetic compositions according to claim 1 and the use of such compositions in cosmetology according to claim 12.

The present invention concerns novel topical formulations which can be used in dermo-cosmetology and more particularly in the treatment of physiological and actinic cutaneous senescence.

These formulations are based on a combination of active ingredients which potentiate collagen regeneration and protection against free radicals.

The active ingredients are chiefly colloidal silver and deoxyribonucleic acid (DNA) optionally in association with caffeine.

Skin Ageing:

Physiological Ageing:

Numerous phenomena are involved: genetic determinism, lifestyle, general condition of the body all add together with age to alter the physical structures and functioning of the skin integument.

The onset of the first sign occurs at around the age of 30 years and affects the elastic fibres of the papillary dermis. The second stage occurs towards the age of 50 and concerns the collagen fibres of the deep dermis.

Actinic Ageing:

The sun aggravates wrinkles and causes the onset of pigmented skin spots.

Examination under the microscope of a skin region subjected to chronic exposure to sun rays (e.g. the face) shows the degeneration induced by ultraviolet rays and the formation of free radicals.

This solar elastosis affects the median part of the dermis where the elastic fibres are irregular and clumped together. Fibres in packets dislocate the bundles of collagen accounting for loss of elasticity and the formation of wrinkles.

Active Ingredients Used:

Dermocosmetic compositions are defined in claim 1 of the present invention and the use of such compositions in cosmetology is defined in claim 12 of the present invention.

The dermocosmetic compositions enclose/contain as active ingredients a synergistic combination of colloidal silver and deoxyribonucleic acid, and are characterized in that the colloidal silver is more particularly an aqueous solution of electro-colloidal silver.

The compositions of the present invention may contain caffeine.

The electro-colloidal silver in the compositions of the present invention may contain 80 to 96% silver ions and 4 to 20% silver particles.

The particle size of the silver may be between 0.0008 and 0.04 microns.

The colloidal silver solution may contain 5 to 20 ppm silver.

The colloidal silver solution may contain 10 ppm silver.

The compositions of the present invention may contain 1 to 90% of colloidal silver.

The deoxyribonucleic acid in the compositions of the present invention may in particular be highly polymerised deoxyribonucleic acid (HP DNA).

The highly polymerised DNA is more particularly HP DNA in the form of a sodium salt.

The compositions of the present invention may contain 0.1 to 5% of HP DNA.

The compositions of the present invention may contain 0.1 to 3% of caffeine.

The compositions of the present invention may be used in cosmetology for the treatment of ageing disorders and more particularly for anti-wrinkle action.

Colloidal Silver:

It is to be pointed out that there are four different products on the market called colloidal silver or silver colloid;

The first type is the conventional product used in our formulations called electro-colloidal silver. This product is prepared using the electric arc method in deionised water, or using a low voltage electrolysis method in distilled water. This product is usually found in a concentration of 3 to 20 ppm. It is formed of microscopic particles of pure elementary silver suspended in water. Each silver particle has a positive electric charge. The silver colloid thus prepared is fully transparent.

The second is called protein silver colloid; this product at chemical level attaches microscopic silver particles to a protein molecule.

The third is the group of silver salts e.g. silver citrate.

The fourth is sometimes called "silver powder". This product was developed by the Russians and is the result of a pure silver wire being disintegrated by a high voltage electric discharge. This microscopic dust is collected and dissolved in water.

Electro-colloidal silver is considered to be a colloid on account of the size of the particles and is considered to be ionic on account of its positive charge.

Most biological studies show that electro-colloidal silver displays better pharmacological action than other silver colloids.

The compositions of the present invention contain 1 to 90% of colloidal silver.

The pharmacological and biological actions of electro-colloidal silver that are of most interest for use in cosmetology are the following:

Anti-Radical and Tissue Regeneration Activity:

Colloidal silver has anti-radical action. Dr. BECKER in 1985 studied the mechanism via which silver ions regenerate the tissues. Silver ions form a complex with living cells to produce stem cells responsible for tissue regeneration.

Anti-bacterial Activity:

New bacteriological tests have shown the efficacy of colloidal silver against pathogenic microorganisms. A study by UCLA in 1988 concludes that it has antibacterial action against pyogenic *Streptococci, staphylococcus aureus*.

Helen BUCKLEY (Temple University Philadelphia 1995) used very small doses of colloidal silver with efficacy on several varieties of *candida albicans* and several *Cryptococci*.

In a study conducted by the Microbiology Institute in Rome and published in Applied and Environmental Microbiology in December 1992, different forms of silver were tested to verify their capability of killing microorganisms. Electro-colloidal silver performed better than silver nitrate, silver chloride and silver sulfadiazine for its ability to act as germicidal with broad spectrum activity on all species of bacteria and fungi.

Action on the Immune System:

Jason HENRY tested colloidal silver on a pathogenic yeast (*S. cerivisae*) and reported that a single application of the product at a dose of 10 ppm was capable of halting the development of the yeast for 24 hours, which enabled the immunity system to have the time to react.

Anti-inflammatory and Analgesic Activities:

The British Medical Journal also reports that colloidal silver has anti-inflammatory and analgesic action.

Toxicology:

Sovereign Silver colloidal silver marketed by Natural Immunogenics, at a dose of 10 ppm was tested in an FDA-approved laboratory (Covance Laboratories Inc.). This toxicological study confirms the perfect tolerance and innocuousness of this product (report dated 20 Mar. 2003).

Deoxyribonucleic Acid:

Deoxyribonucleic acid (DNA) is a molecule well known to biologists since the work by WATSON and CRIK (NOBEL Prize).

The DNA used in our formulations is more particularly highly polymerised DNA in its sodium salt form marketed by JAVENECH.

This macromolecule of marine origin is in the form of long white fibres. This fibrous appearance is characteristic of the super double helix organisation of this bio-polymer.

The extraction of HP (highly polymerised) DNA using non-denaturing techniques ensures full protection of the molecular structure preserving its physiological activity.

The Main Biological Characteristics of HP DNA are the Following:

Hydrating Action:

HP DNA is an excellent skin hydrating agent. At cell level, when the HP DNA molecules are diffused, they bind to a volume of aqueous solution greater than 10 000 times their own volume.

The compositions of the present invention contain 0.1 to 5% of HP DNA.

Anti-oxidizing Action:

By trapping ° OH radicals inside the double helix: the HP DNA biomolecule has the advantage compared with most other substances of same activity of not generating a derivative, after free radical capture, that is likely to deteriorate other neighbouring constituents.

The ° OH radical attaches to the bases of the molecule and in particular on guanine to give a stable compound: 8 hydroxyguanoside.

Its anti-lipoperoxidating properties (trapping of ° OH radicals involved in the initiation of lipid peroxidation) can be used to advantage to protect membrane lipids of the skin against oxidation, and in creams to protect the oil phase.

HP DNA is also able to inhibit elastases and more particularly the elastase of human skin fibroblasts primarily responsible for lysis of the elastic fibres of the dermis over the course of ageing.

Healing Action:

This activity is evidenced on corneal wounds, hence its excellent tolerance for ocular mucosa (use in <<eye contour>> products).

Added to the biological effects of HP DNA is a major physical characteristic which reinforces its protective role for skin structures. Under a narrow thickness of 1 mm, a 1% solution of HPA DNA entirely absorbs low intensity UV rays of between 200 and 300 nm, which is the radiation that damages cellular DNA.

Experiments performed in vitro have shown that HP DNA stimulates the synthesis of collagens and proteoglycans.

Caffeine:

This product is used in our formulations for its lipolytic effect, more particularly in <<eye contour>> formulations which have good anti-dark circle action.

The compositions of the present invention contain 0.1 to 3% caffeine.

Combination of Colloidal Silver and HP DNA

The synergistic actions of the combination of colloidal silver and HP DNA according to the invention have been demonstrated in vitro and in vivo in the following indications:

Anti-radical Action (In vitro):

Lipid peroxidation is a typical case of a chain reaction induced by radical route. The oxidation of membrane lipids leads to the formation of lipid peroxides which decompose into different fragmentation products of which some are highly toxic and harsh for the skin.

One of the most important and most aggressive fragmentation products is an aldehyde, malone dialdehyde (MDA) which displays formidable toxicity via the cross-bridging of proteins, intracellular lipids and DNA.

It therefore appears that free radicals and the cascaded chain reaction they cause within the body play an essential role in the process of skin ageing.

With the objective of combating this radical action, the applicant proposes a combination of colloidal silver and HP DNA.

For this purpose, each of the two active ingredients was subjected to the following treatment of initiated lipid peroxidation:

peroxidation of a linoleic acid emulsion was induced by ° OH hydroxyl radicals;

a synergistic effect (gain in protection observed ranging from 54% to 215% compared with an additive effect). This synergistic action is more particularly pronounced with a quantity of 65 to 80 ml of 10 ppm colloidal silver containing 0.3 to 0.5% HP DNA.

Collagen Regeneration (In vitro Cell Culture):

UV rays perturb cell metabolism, in particular fibroblast metabolism.

Fibroblasts taken from a skin region and exposed to UV radiation lose their capacity to synthesise macromolecules and more particularly collagen, according to the work conducted by OIKARINEN et al: Connective tissue alteration in skin exposed to natural and therapeutic UV radiations. Photodermatology 2, p. 15-26 (1985).

Under these experimental conditions, strong potentiation was observed of collagen regeneration with the association of colloidal silver and HP DNA.

The most interesting results (65% to 185% regeneration compared with an additive effect) were observed with a quantity of 60 ml to 80 ml of 10 ppm colloidal silver containing 0.3% to 0.5% HP DNA.

Clinical Studies: Anti-wrinkle Action

The formulation in Example 1 was tested clinically using a method to assess anti-wrinkle activity.

The method used was the skin imprint technique associated with macro-photographic analysis.

The results of this study, conducted in 78 women aged 30 to 82 years for three months, are given as % wrinkle reduction in the following table.

% Wrinkle Reduction

|  | Time | | |
| --- | --- | --- | --- |
|  | 1 month | 2 months | 3 months |
| Light wrinkles | 37% | 64% | 88% |
| Mid-depth wrinkles | 21% | 38% | 67% |
| Deep wrinkles | 15% | 26% | 39% |

The results with HP DNA alone at a dose of 500 mg in the excipients of the cream in Example 1 are the following:

% Wrinkle Reduction

|  | Time | | |
| --- | --- | --- | --- |
|  | 1 month | 2 months | 3 months |
| Light wrinkles | 9% | 12% | 17% |
| Mid-depth wrinkles | 7% | 9% | 11% |
| Deep wrinkles | 2% | 3% | 3% |

The results with 70 ml of colloidal silver at a dose of 10 ppm in the excipients of the cream in Example 1 are the following:

% Wrinkle Reduction

|  | Time | | |
| --- | --- | --- | --- |
|  | 1 month | 2 months | 3 months |
| Light wrinkles | 12% | 16% | 22% |
| Mid-depth wrinkles | 9% | 10% | 12% |
| Deep wrinkles | 3% | 5% | 6% |

These results confirm the very strong potentiation of the anti-wrinkle action of colloidal silver in combination with HP DNA.

Having regard to these results, the Applicant proposes cosmetic compositions containing a synergistic combination of colloidal silver and HP DNA which can be used in the treatment of physiological and actinic skin ageing, optionally in association with caffeine.

The colloidal silver used is electro-colloidal silver containing 80 to 96% $Ag^+$ ionic silver and 4 to 20% of particles. The particle size of the silver varies from 0.0008 microns to 0.04 microns.

The ppm content (parts per million) of the colloidal silver solution is between 5 ppm and 20 ppm.

It is also to be noted that the strong concentrations of colloidal silver solution allow a significant reduction in the amount of preserving agents in our cosmetic formulations.

The colloidal silver used is more particularly the silver marketed by Natural Immunogenics at a dose of 10 ppm.

The DNA used is more particularly highly polymerised (HP) DNA in sodium salt form marketed by JAVENECH.

The topical formulations of the novel combination of active ingredients according to the present invention are illustrated by the following non-limiting examples:

EXAMPLE 1

O/W Fluid Emulsion for Mixed Skins

| Active ingredients: | 70 to 80 ml of 10 ppm colloidal silver solution |
| --- | --- |
| HP DNA: | 500 mg |
| Caffeine: | 500 mg |
| Natural excipients of vegetable origin: | |
| Organic sweet almond oil | 1 to 5% |
| Organic argan oil: | 1 to 5% |
| Organic shea butter: | 1 to 5% |
| Organic aloe vera oil extract: | 1 to 5% |
| Cetearyl alcohol, cetearyl glucoside: | 5 to 10% |
| Hydrogenated vegetable glycerides: | 1 to 5% |
| Glycerine: | 1 to 5% |
| Dicaprylyl carbonate: | 1 to 5% |
| Caprylic/capric triglycerides: | 1 to 5% |
| Sodium stearoyl glutamate: | less than 1% |
| Tocopheryl acetate: | less than 1% |
| Xanthan gum: | less than 1% |
| ECOCERT preserving agents: | less than 1% |
| Hypoallergenic perfume: | less than 1%. |

EXAMPLE 2

Cream for Dry Skin

| Active ingredients: | 60 to 80 ml of 10 ppm colloidal silver solution |
| --- | --- |
| HP DNA: | 900 to 1000 mg |
| ECOCERT preserving agents: | less than 1% |
| Hypoallergenic perfume: | less than 1% |
| Other natural excipients of vegetable origin: | to 100 g. |

EXAMPLE 3

Cream for Greasy Skin

| Active ingredients: | 65 to 85 ml of 10 ppm colloidal silver solution |
| --- | --- |
| HP DNA: | 800 mg |
| Caffeine: | 750 mg |
| ECOCERT preserving agents: | less than 1% |
| Hypoallergenic perfume: | less than 1% |
| Other natural excipients of vegetable origin: | to 100 g. |

EXAMPLE 4

Facial Cleanser

| Active ingredients: | 60 to 80 ml of 10 ppm colloidal silver solution |
| --- | --- |
| HP DNA: | 350 mg |
| ECOCERT preserving agents: | less than 1% |
| Hypoallergenic perfume: | less than 1% |
| Other natural excipients of vegetable origin: | to 100 ml. |

EXAMPLE 5

Astringent

| Active ingredients: | 70 to 80 ml of 10 ppm colloidal silver solution |
| --- | --- |
| HP DNA: | 250 mg |
| ECOCERT preserving agents: | less than 1% |
| Hypoallergenic perfume: | less than 1% |
| Other natural excipients of vegetable origin: | to 100 ml. |

EXAMPLE 6

Eye Contour Cream

| | |
|---|---|
| Active ingredients: | 60 to 80 ml of 10 ppm colloidal silver solution |
| HP DNA: | 1000 to 1200 mg |
| Caffeine: | 500 to 800 mg |
| ECOCERT preserving agents: | less than 1% |
| Hypoallergenic perfume: | less than 1% |
| Other natural excipients of vegetable origin: | to 100 g. |

EXAMPLE 7

Lip Balm

| | |
|---|---|
| Active ingredients: | 2 to 5 ml of 20 ppm colloidal silver solution |
| HP DNA: | 500 to 900 mg |
| ECOCERT preserving agents: | less than 1% |
| Hypoallergenic perfume: | less than 1% |
| Other natural excipients of vegetable origin: | to 100 g. |

EXAMPLE 8

Liquid Soap

| | |
|---|---|
| Active ingredients: | 70 to 90 ml of 20 ppm colloidal silver solution |
| HP DNA: | 300 to 500 mg |
| Caffeine: | 300 to 500 mg |
| ECOCERT preserving agents: | less than 1% |
| Hypoallergenic perfume: | less than 1% |
| Other natural excipients of vegetable origin: | to 100 ml. |

EXAMPLE 9

Soap

| | |
|---|---|
| Active ingredients: | 1 to 5 ml of 15 ppm colloidal silver solution |
| HP DNA: | 100 to 200 mg |
| ECOCERT preserving agents: | less than 1% |
| Hypoallergenic perfume: | less than 1% |
| Other natural excipients of vegetable origin: | to 100 g. |

EXAMPLE 10

Hydrating Hand Cream

| | |
|---|---|
| Active ingredients: | 60 to 90 ml of 10 ppm colloidal silver solution |
| HP DNA: | 200 to 500 mg |
| ECOCERT preserving agents: | less than 1% |
| Hypoallergenic perfume: | less than 1% |
| Other natural excipients of vegetable origin: | to 100 g. |

EXAMPLE 11

Bath/Shower

| | |
|---|---|
| Active ingredients: | 70 to 90 ml of 10 ppm colloidal silver solution |
| HP DNA: | 100 to 200 mg |
| ECOCERT preserving agents: | less than 1% |
| Hypoallergenic perfume: | less than 1% |
| Other natural excipients of vegetable origin: | to 100 ml. |

EXAMPLE 12

Hydrating Body Milk

| | |
|---|---|
| Active ingredients: | 65 to 85 ml of 10 ppm colloidal silver solution |
| HP DNA: | 500 to 1000 mg |
| ECOCERT preserving agents: | less than 1% |
| Hypoallergenic perfume: | less than 1% |
| Other natural excipients of vegetable origin: | to 100 ml. |

EXAMPLE 13

Bath Oil

| | |
|---|---|
| Active ingredients: | 1 to 3 ml of 10 ppm colloidal silver solution |
| HP DNA: | 100 to 200 mg |
| ECOCERT preserving agents: | less than 1% |
| Hypoallergenic perfume: | less than 1% |
| Other natural excipients of vegetable origin: | to 100 ml. |

EXAMPLE 14

Sun Cream

| | |
|---|---|
| Active ingredients: | 65 to 80 ml of 10 ppm colloidal silver solution |
| HP DNA: | 100 to 1500 mg |
| ECOCERT preserving agents: | less than 1% |
| Hypoallergenic perfume: | less than 1% |
| Other natural excipients of vegetable origin: | to 100 g. |

EXAMPLE 15

Soothing after-Sun Milk

| | |
|---|---|
| Active ingredients: | 70 to 80 ml of 15 ppm colloidal silver solution |
| HP DNA: | 500 to 750 mg |
| ECOCERT preserving agents: | less than 1% |
| Hypoallergenic perfume: | less than 1% |

EXAMPLE 16

Cold Cream

| | |
|---|---|
| Active ingredients: | 5 to 10 ml of 20 ppm colloidal silver solution |
| HP DNA: | 300 to 500 mg |
| ECOCERT preserving agents: | less than 1% |
| Hypoallergenic perfume: | less than 1% |
| Other natural excipients of vegetable origin: | to 100 g. |

EXAMPLE 17

Tan-Colour Tinted Cream

| | |
|---|---|
| Active ingredients: | 65 to 80 ml of 10 ppm colloidal silver solution |
| HP DNA: | 300 to 500 mg |
| ECOCERT preserving agents: | less than 1% |
| Hypoallergenic perfume: | less than 1% |
| Other natural excipients of vegetable origin: | to 100 g. |

EXAMPLE 18

Eau De Toilette

| | |
|---|---|
| Active ingredients: | 30 to 50 ml of 5 ppm colloidal silver solution |
| HP DNA: | 100 to 250 mg |
| Hypoallergenic perfume: | less than 1% |
| Ethyl alcohol, 95°: | to 100 ml. |

The invention claimed is:

1. A dermocosmetic composition comprising:
   a highly polymerized deoxyribonucleic acid ("HP DNA") in sodium salt form; and
   an aqueous solution of electro-colloidal silver, wherein the aqueous solution of electro-colloidal silver comprises 5-20 ppm electro-colloidal silver, and wherein the electro-colloidal silver comprises 80-96% by weight silver ions and 4-20% by weight silver particles, wherein the dermocosmetic composition comprises 0.1 to 5% HP DNA;
   wherein the dermocosmetic composition comprises 1-90% by weight of the aqueous solution of electro-colloidal silver; and
   wherein the HP DNA and the aqueous solution of electro-colloidal silver are present at a ratio that synergistically increases at least one of protection against peroxidation of linoleic acid by 54-215% above an additive protective effect and collagen regeneration by 65-185% above an additive regeneration effect.

2. The dermocosmetic composition according to claim 1, further comprising caffeine.

3. The dermocosmetic composition according to claim 1, wherein the silver particles are between 0.0008 and 0.04 microns.

4. The dermocosmetic composition according to claim 1, wherein the aqueous solution of electro-colloidal silver comprises 10 ppm silver.

5. The dermocosmetic composition according to claim 2, wherein the dermocosmetic composition comprises 0.1 to 3% caffeine.

6. The dermocosmetic composition to claim 1, characterized in that it can be applied to skin for the treatment of ageing disorders and for anti-wrinkle action.

7. A method of treating a human for an ageing disorder comprising providing a dermocosmetic composition according to claim 1 in a therapeutically effective amount.

8. A method of reducing wrinkles in a human comprising providing a dermocosmetic composition according to claim 1 in an amount effective to reduce a wrinkle depth in the human.

* * * * *